(12) United States Patent
Ota

(10) Patent No.: US 12,397,732 B2
(45) Date of Patent: Aug. 26, 2025

(54) ILLUMINATION CONTROL DEVICE, BIOMETRIC INFORMATION ACQUIRING DEVICE, AND ILLUMINATION CONTROL METHOD

(71) Applicant: Mitsubishi Electric Corporation, Tokyo (JP)

(72) Inventor: Shuhei Ota, Tokyo (JP)

(73) Assignee: MITSUBISHI ELECTRIC CORPORATION, Tokyo (JP)

( * ) Notice: Subject to any disclaimer, the term of this patent is extended or adjusted under 35 U.S.C. 154(b) by 26 days.

(21) Appl. No.: 18/292,614

(22) PCT Filed: Sep. 24, 2021

(86) PCT No.: PCT/JP2021/034932
§ 371 (c)(1),
(2) Date: Jan. 26, 2024

(87) PCT Pub. No.: WO2023/047505
PCT Pub. Date: Mar. 30, 2023

(65) Prior Publication Data
US 2024/0336215 A1    Oct. 10, 2024

(51) Int. Cl.
*B60R 21/01*    (2006.01)
*B60Q 3/70*    (2017.01)
(Continued)

(52) U.S. Cl.
CPC .......... *B60R 21/01538* (2014.10); *B60Q 3/70* (2017.02); *G06V 40/103* (2022.01);
(Continued)

(58) Field of Classification Search
CPC .... B60R 21/01538; B60R 2021/01006; B60R 2021/01013; B60Q 3/70; B60Q 2500/30;
(Continued)

(56) References Cited

U.S. PATENT DOCUMENTS 9,208,526 B1 * 12/2015 Leise .................. G07C 5/00
9,857,456 B2 * 1/2018 Hara .................. G01S 17/931
(Continued)

FOREIGN PATENT DOCUMENTS

DE    102020000531 A1 * 10/2020    .............. B60Q 3/80
JP    2003-306106 A    10/2003
(Continued)

OTHER PUBLICATIONS

International Search Report, issued in PCT/JP2021/034932, PCT/ISA/210, dated Dec. 21, 2021.

*Primary Examiner* — Joseph J Dallo
(74) *Attorney, Agent, or Firm* — Birch, Stewart, Kolasch & Birch, LLP

(57) ABSTRACT

An illumination control device includes: an accident detection unit to detect an accident of a vehicle using a signal output from a sensor mounted on the vehicle; a lamp body control unit to command a lamp body that illuminates a vehicle interior using visible light to turn on when an accident is detected by the accident detection unit; and a lamp color changing unit to change a lamp color of the lamp body when the accident is detected by the accident detection unit.

9 Claims, 12 Drawing Sheets

(51) Int. Cl.
*B60R 21/015* (2006.01)
*G06V 40/10* (2022.01)

(52) U.S. Cl.
CPC .......... *G06V 40/15* (2022.01); *B60Q 2500/30* (2022.05); *B60R 2021/01006* (2013.01); *B60R 2021/01013* (2013.01)

(58) Field of Classification Search
CPC .......... B60Q 3/76; B60Q 3/80; G06V 40/103; G06V 40/15; G06V 20/59; A61B 5/02; A61B 5/08; A61B 5/0077; Y02B 20/40
See application file for complete search history.

(56) References Cited

U.S. PATENT DOCUMENTS

| | | | | |
|---|---|---|---|---|
| 10,121,380 | B2* | 11/2018 | Rajendran | G06V 20/56 |
| 10,281,900 | B2* | 5/2019 | Kubo | G05B 19/406 |
| 10,282,922 | B1* | 5/2019 | Nejah | G08B 25/10 |
| 10,417,913 | B2* | 9/2019 | Panigrahi | B60R 21/0134 |
| 10,796,376 | B2* | 10/2020 | Aznaurashvili | G06Q 50/265 |
| 10,819,943 | B2* | 10/2020 | Van Dan Elzen | H04N 23/66 |
| 10,919,475 | B2* | 2/2021 | Panigrahi | B60R 21/0136 |
| 11,203,316 | B2* | 12/2021 | Halford | B60R 21/0136 |
| 11,302,123 | B2* | 4/2022 | Nozawa | G07C 5/0866 |
| 11,335,135 | B2* | 5/2022 | Zwissler | G07C 5/085 |
| 11,743,373 | B2* | 8/2023 | Katayama | H04M 1/72421 |
| | | | | 455/404.1 |
| 2010/0272510 | A1* | 10/2010 | Mohajer | E01F 9/559 |
| | | | | 362/249.02 |
| 2014/0375446 | A1* | 12/2014 | Wanami | G08G 1/205 |
| | | | | 340/436 |
| 2019/0297234 | A1 | 9/2019 | Nagahama et al. | |
| 2020/0290542 | A1 | 9/2020 | Nakamura et al. | |

FOREIGN PATENT DOCUMENTS

| | | | | |
|---|---|---|---|---|
| JP | 2015-5075 | A | 1/2015 | |
| JP | 2015-64764 | A | 4/2015 | |
| JP | 2018-19020 | A | 2/2018 | |
| JP | 2018-136859 | A | 8/2018 | |
| JP | 2020-149650 | A | 9/2020 | |
| JP | 2020-177444 | A | 10/2020 | |
| WO | WO-2012170953 | A2* | 12/2012 | G01N 21/17 |
| WO | WO-2014147494 | A1* | 9/2014 | H05B 47/22 |
| WO | WO-2022045258 | A1* | 3/2022 | B60N 2/879 |

* cited by examiner

FIG. 2

| Type of Biometric Information | Lamp Color | R | G | B |
|---|---|---|---|---|
| Pulse | Green | ... | ... | ... |
| Complexion | White | ... | ... | ... |
| Bleeding State | * | ... | ... | ... |
| Respiration | * * | ... | ... | ... |
| ... | ... | ... | ... | ... |

| Type of Biometric Information | Site 1 | Site 2 | Site 3 | Site 4 | ... |
|---|---|---|---|---|---|
| Pulse | Head | Neck | — | — | ... |
| Complexion | Head | — | — | — | ... |
| Bleeding State | Head | Neck | Chest | Arm | ... |
| Respiration | Head | Neck | Chest | — | ... |
| ... | ... | ... | ... | ... | ... |

700

ILLUMINATION CONTROL DEVICE, BIOMETRIC INFORMATION ACQUIRING DEVICE, AND ILLUMINATION CONTROL METHOD

TECHNICAL FIELD

The present disclosure relates to an illumination control technique of controlling illumination to a vehicle interior.

BACKGROUND ART

Conventionally, there is a technique of lighting an illumination device when imaging a vehicle interior.

For example, Patent Literature 1 discloses a technique of lighting an illumination device such as an indoor light or an imaging light attached to a camera in advance depending on brightness and darkness in a vehicle interior in an emergency notification device that images an occupant when a vehicle accident occurs and transmits an imaged image to an emergency center. In the conventional technique described in Patent Literature 1, imaging can be performed even in a dark case by lighting the illumination device when a vehicle accident occurs. The imaged image is used to visually recognize a situation of the occupant in the emergency center.

CITATION LIST

Patent Literature

Patent Literature 1: JP 2003-306106 A

SUMMARY OF INVENTION

Technical Problem

In the conventional technique described in Patent Literature 1, since the illumination device is simply lighted and illumination is performed using light of a certain color, there is a problem that there is biometric information that cannot be obtained from an imaged image under some imaging conditions when a vehicle accident occurs.

The present disclosure has been made in order to solve the above problem, and an object of the present disclosure is to provide an illumination control technique of controlling illumination in such a manner that biometric information can be obtained without depending on imaging conditions when a vehicle accident occurs.

Solution to Problem

An illumination control device of the present disclosure includes: processing circuitry configured to detect an accident of a vehicle using a signal output from a sensor mounted on the vehicle; command a lamp body that illuminates a vehicle interior using visible light to turn on when an accident is detected; and change a lamp color of the lamp body when an accident is detected; command an imaging device that performs imaging using visible light to image a vehicle interior when the accident is detected; specify a position of a site of a living body in the vehicle interior using an imaged image acquired in response to the command; and estimate the position of the site of the living body in the vehicle interior and command the lamp body to adjust light distribution with respect to the estimated position of the site of the living body when the position of the site of the living body in the vehicle interior is not specified.

Advantageous Effects of Invention

According to the present disclosure, it is possible to provide an illumination control device that controls illumination in such a manner that biometric information can be obtained without depending on imaging conditions when a vehicle accident occurs.

BRIEF DESCRIPTION OF DRAWINGS

FIG. 2 is a diagram illustrating an example of a correspondence relationship between a type of biometric information and a lamp color.

FIG. 3 is a diagram illustrating an example of a correspondence relationship between a type of biometric information and a site of a living body.

DESCRIPTION OF EMBODIMENTS

Hereinafter, in order to describe the present disclosure in more detail, embodiments for carrying out the present disclosure will be described with reference to the attached drawings.

First Embodiment

Figure 1:
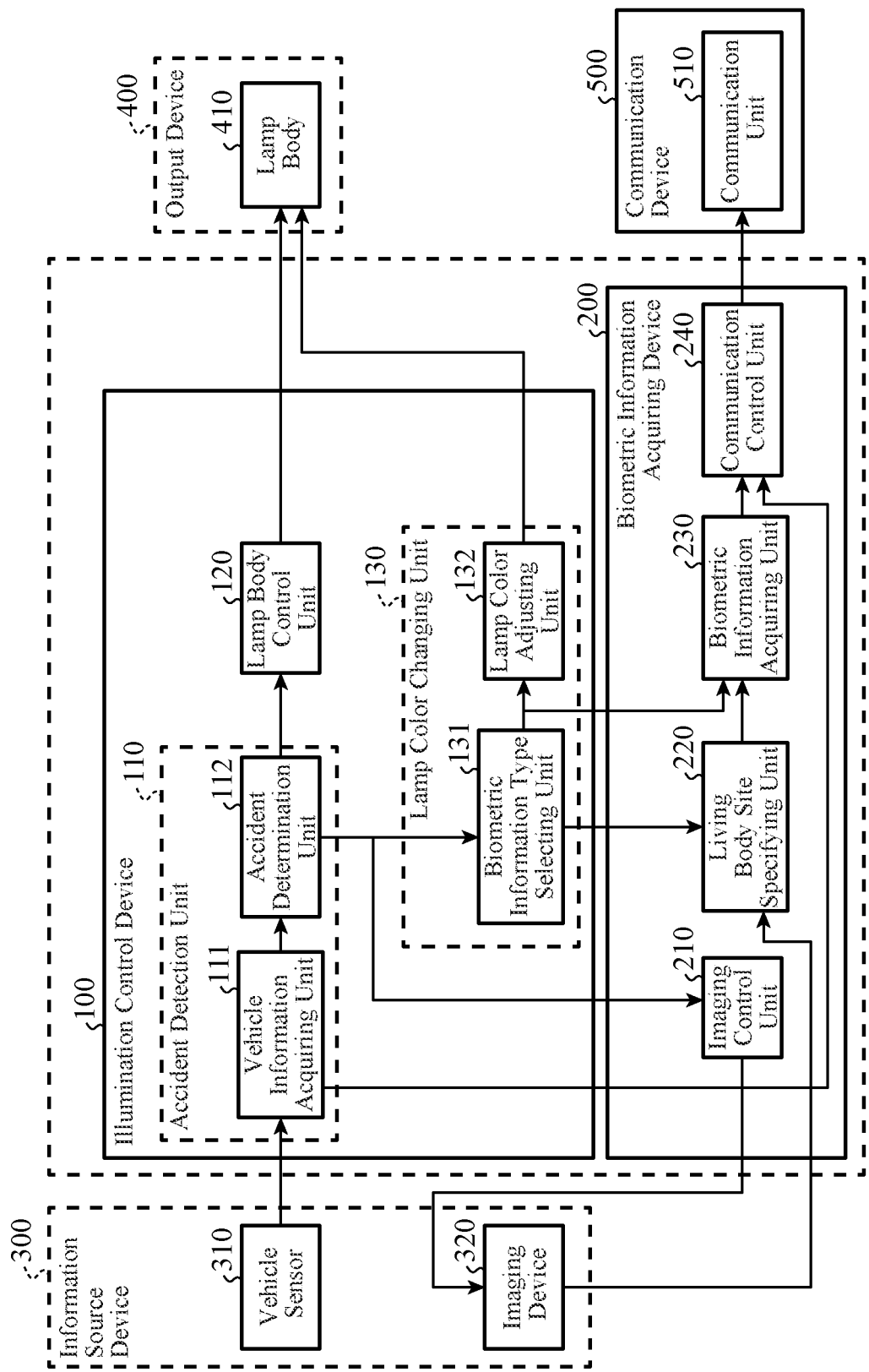
FIG. 1 is a block diagram illustrating a configuration of an illumination control device according to a first embodiment and a peripheral device related thereto.

FIG. 1 is a block diagram illustrating a configuration of an illumination control device 100 according to a first embodiment and a peripheral device related thereto.

The illumination control device 100 controls illumination of a vehicle interior by commanding a lamp body 410 that illuminates the vehicle interior to turn on the lamp body 410 and designating a lamp color. In particular, the illumination control device 100 of the present disclosure issues a command to change a lamp color of the lamp body 410 when an accident of a vehicle occurs.

The illumination control device 100 illustrated in FIG. 1 is communicably connected to a biometric information acquiring device 200, an information source device 300, and an output device 400.

An example of a detailed configuration of the illumination control device 100 will be described later.

The biometric information acquiring device 200 acquires biometric information using an imaged image that is an image obtained by imaging a vehicle interior, and outputs the acquired biometric information.

The biometric information in the present disclosure is biometric information that can be acquired using an imaged image, and is, for example, a pulse, a complexion, a bleeding state, respiration, or the like.

The biometric information acquiring device 200 illustrated in FIG. 1 is communicably connected to the illumination control device 100, the information source device 300, and a communication device 500.

An example of a detailed configuration of the biometric information acquiring device 200 will be described later.

The information source device 300 is a device that provides information used for a process by the illumination control device 100 or the biometric information acquiring device 200.

Specifically, the information source device 300 includes a vehicle sensor 310 and an imaging device 320 mounted on a vehicle.

The vehicle sensor 310 outputs a signal related to vehicle information.

The vehicle information in the present disclosure is information that makes it possible to determine an accident of a vehicle, a state related to the vehicle, a situation of a vehicle interior, and the like.

The vehicle information is, for example, a vehicle speed, an acceleration, vehicle position information, seat sensor information, light sensor information, parking brake information, vehicle device failure notification information, or airbag operation notification information.

The vehicle sensor 310 is constituted by a plurality of sensors that outputs a signal related to the vehicle information.

Note that the vehicle sensor 310 may transmit a signal related to the vehicle information via an electronic control unit (ECU) (not illustrated) without directly transmitting a signal related to the vehicle information. The ECU is a control unit that controls each main operation of a vehicle. The ECU is connected to the illumination control device 100 by a wire harness (not illustrated), and can freely communicate with the illumination control device 100 by a communication method based on a controller area network (CAN) standard.

The imaging device 320 is disposed at a position where a vehicle interior can be imaged, and images the vehicle interior.

The imaging device 320 includes a first imaging element that converts visible light into an electrical signal, and outputs a visible light imaged image that is an image obtained by imaging the vehicle interior by the first imaging element receiving the visible light. The visible light imaged image is hereinafter simply referred to as an "imaged image".

The imaging device 320 in the present disclosure images the vehicle interior in response to a command from an imaging control unit 210.

In the first embodiment, specifically, when an accident of the vehicle occurs, the imaging device 320 receives a command from the imaging control unit 210 of the biometric information acquiring device 200 and images the vehicle interior.

Here, for example, a camera included in a driver monitoring system (DMS) may be used as the imaging device 320.

In this case, the imaging device 320 images occupants including a driver in the vehicle interior.

When the camera included in the DMS is used, the imaging device 320 may include a second imaging element that converts infrared light into an electrical signal, and may have a function of outputting an infrared imaged image that is an image obtained by imaging the vehicle interior by the second imaging element receiving the infrared light. The infrared imaged image is hereinafter referred to as an "infrared image" in order to be distinguished from an imaged image that is a visible light imaged image.

In this case, the imaging device 320 images infrared light and outputs an infrared image in a state where no vehicle accident occurs, and switches to visible light imaging by receiving a command from the imaging control unit 210, and outputs an imaged image when a vehicle accident occurs.

Note that the imaging device 320 may transmit an image via an electronic control unit (ECU) (not illustrated) without directly transmitting an image (imaged image or infrared image). The ECU is a control unit that controls each main operation of a vehicle. The ECU is connected to the biometric information acquiring device 200 or the illumination control device 100 by a wire harness (not illustrated), and can freely communicate with the biometric information acquiring device 200 or the illumination control device 100 by a communication method based on a controller area network (CAN) standard.

The output device 400 is a control target device to which a command is issued from the illumination control device 100 of the present disclosure, and is specifically the lamp body 410.

The lamp body 410 is included in, for example, a vehicle interior illumination device, and illuminates the vehicle interior using visible light.

The lamp body 410 is, for example, a room lamp, a map lamp, a foot lamp, a side step lamp, a door lamp, or an ambient lamp.

The room lamp is the lamp body 410 that illuminates the entire vehicle interior. and is disposed, for example, on a ceiling portion of the vehicle interior.

The map lamp is, for example, the lamp body 410 disposed for a driver's seat or an assistant driver's seat.

The foot lamp is the lamp body 410 disposed in such a way as to illuminate feet of an occupant.

The side step lamp is the lamp body 410 incorporated in a side step.

The door lamp is the lamp body 410 incorporated in a door.

The ambient lamp is a decorative lamp body incorporated in a dashboard, a center console, an edge of a side door, or the like.

The lamp body 410 in the present disclosure may include all of the lamp bodies or some of the lamp bodies.

The lamp body 410 illustrated in FIG. 1 switches between a lamp-on state and a lamp-off state in response to a command issued from the illumination control device 100.

The lamp body 410 also changes a lamp color in response to a command issued from the illumination control device 100.

Specifically, the lamp body 410 includes, for example, a light source obtained by aggregating a plurality of light emitting diodes (LEDs).

As for the plurality of LEDs in the lamp body 410, for example, three LEDs emit light beams having different wavelengths (for example, three primary colors of light (R, G, and B) such as red, green, and blue), respectively, and a wavelength component or a ratio of an intensity of each of the light beams can be changed in response to a command issued from the illumination control device 100.

When an LED is used for the lamp body 410, for example, power consumption can be reduced and a life thereof is longer as compared with a case where a lamp (for example, a halogen lamp) other than the LED is used. In addition, fine illumination control is possible.

Illumination control in the present disclosure includes control of a lamp color, control of brightness, and control of light distribution.

The control of a lamp color is, for example, to cause various colors to be output by adjusting and combining brightness values of the colors of RGB.

The control of light distribution includes control of a light irradiation range and control of light directivity.

The control of light distribution can be implemented by, for example, a method for lighting only some of the plurality of LEDs in the lamp body 410 without lighting all of the LEDs.

The communication device 500 communicates with the outside of the vehicle.

The communication device 500 performs, for example, wireless communication with an external device that collects information from a plurality of vehicles.

The communication device 500 illustrated in FIG. 1 is a mode in which vehicle information acquired by a vehicle information acquiring unit 111 from the vehicle sensor 310 and biometric information acquired by the biometric information acquiring device 200 are transmitted to a server (not illustrated) via a communication unit 510.

Details of the illumination control device 100 will be described.

The illumination control device 100 includes an accident detection unit 110, a lamp body control unit 120, and a lamp color changing unit 130.

In addition to the above components, the illumination control device 100 includes a control unit (not illustrated) and a storage unit (not illustrated). The control unit (not illustrated) controls, for example, the entire device including the components. The storage unit (not illustrated) stores, for example, information used in processes performed by the components or information generated in the processes.

The accident detection unit 110 detects an accident of a vehicle using a signal output from the vehicle sensor 310 mounted on the vehicle.

A method for detecting an accident of the vehicle using a signal from the vehicle sensor 310 can be implemented by a method using a known technique on the basis of a vehicle speed, an acceleration, vehicle position information, seat sensor information, light sensor information, parking brake information, vehicle device failure notification information, or airbag operation notification information.

When detecting an accident of the vehicle, the accident detection unit 110 outputs an accident occurrence signal that is a signal indicating that an accident has occurred.

When detecting an accident of the vehicle, the accident detection unit 110 outputs vehicle information indicated by the signal output from the vehicle sensor 310.

An example of a detailed configuration of the accident detection unit 110 will be described later.

When an accident is detected by the accident detection unit 110, the lamp body control unit 120 commands the lamp body 410 that illuminates the vehicle interior using visible light to turn on the lamp body 410.

Specifically, when receiving an accident detection signal that is a signal indicating that occurrence of an accident has been detected from the accident detection unit 110, the lamp body control unit 120 outputs a lamp-on command signal that is a signal for commanding the lamp body 410 to turn on the lamp body 410.

When an accident is detected by the accident detection unit 110, the lamp color changing unit 130 changes a lamp color of the lamp body 410.

FIG. 2 is a diagram illustrating an example of a correspondence relationship between a type of biometric information and a lamp color.

The lamp color changing unit 130 executes a process by referring to, for example, first data 600 as illustrated in FIG. 2. The first data 600 is information indicating a correspondence relationship between a type of biometric information and a lamp color, and is stored in advance in the storage unit (not illustrated).

The lamp color changing unit 130 selects a type of biometric information and determines a lamp color by referring to the first data 600. The lamp color changing unit 130 changes the lamp color of the lamp body 410 to the determined lamp color.

An example of a detailed configuration of the lamp color changing unit 130 will be described later.

A specific example of a detailed configuration of the accident detection unit 110 will be described.

The accident detection unit 110 includes the vehicle information acquiring unit 111 and an accident determination unit 112.

The vehicle information acquiring unit 111 acquires a signal output from the vehicle sensor 310.

The vehicle information acquiring unit 111 acquires vehicle information using the acquired signal, and outputs the vehicle information to the accident determination unit 112. In addition, the vehicle information acquiring unit 111 outputs the vehicle information to a communication control unit 240.

The accident determination unit 112 determines occurrence of an accident using the vehicle information. When determining that an accident has occurred, the accident determination unit 112 outputs an accident detection signal that is a signal indicating that occurrence of an accident has been detected.

The accident determination unit 112 may output the vehicle information used for the determination together with the accident detection signal.

The accident determination unit 112 may determine a type of accident using the vehicle information. The accident determination unit 112 that performs this determination outputs accident type information indicating the determined type of accident.

A specific example of a detailed configuration of the lamp color changing unit 130 will be described.

The lamp color changing unit 130 includes a biometric information type selecting unit 131 and a lamp color adjusting unit 132.

When an accident is detected by the accident detection unit 110, the biometric information type selecting unit 131 selects a type of biometric information to be acquired by referring to type information indicating a type of biometric information stored in advance.

Specifically, for example, when receiving an accident detection signal from the accident detection unit 110, the biometric information type selecting unit 131 sequentially selects a type of biometric information to be acquired by referring to the type information.

Alternatively, for example, when receiving an accident detection signal from the accident detection unit 110, the biometric information type selecting unit 131 selects all types of biometric information to be acquired by referring to the type information.

The biometric information type selecting unit 131 transmits information indicating the selected type to the lamp color adjusting unit 132. In addition, the biometric information type selecting unit 131 transmits information indicating the selected type to a living body site specifying unit 220 described later.

The lamp color adjusting unit 132 adjusts the lamp color of the lamp body 410 depending on the type of biometric information selected by the biometric information type selecting unit 131.

For example, the lamp color adjusting unit 132 determines the lamp color of the lamp body 410 depending on the type of biometric information by referring to the first data 600 illustrated in FIG. 2, and transmits a command signal for commanding the lamp body 410 to turn on the lamp body 410 with the determined lamp color.

For example, when the type of biometric information selected by the biometric information type selecting unit 131 is a pulse, the lamp color adjusting unit 132 performs adjustment in such a manner that a wavelength of the lamp color is equal to or more than 490 nm and equal to or less than 570 nm. As a result, the lamp color is so-called green, and the lamp body 410 irradiates a living body with green light.

In addition, for example. when the type of biometric information selected by the biometric information type selecting unit 131 is a complexion, the lamp color adjusting unit 132 performs adjustment in such a manner that the lamp color is white. For example, the lamp body 410 is commanded to perform so-called all lamps-on. As a result, the lamp color is so-called white, and the lamp body 410 irradiates a living body with white light.

A specific example of a detailed configuration of the biometric information acquiring device 200 will be described.

The biometric information acquiring device 200 illustrated in FIG. 1 includes the imaging control unit 210, the living body site specifying unit 220, a biometric information acquiring unit 230, and the communication control unit 240.

In addition to the above components, the biometric information acquiring device 200 includes a control unit (not illustrated) and a storage unit (not illustrated). The control unit (not illustrated) controls, for example, the entire device including the components. The storage unit (not illustrated) stores, for example, information used in processes performed by the components or information generated in the processes.

When a vehicle accident occurs, the imaging control unit 210 commands the imaging device 320 to perform imaging.

Specifically, when an accident is detected by the accident detection unit 110. the imaging control unit 210 commands the imaging device 320 that performs imaging by receiving visible light to image the vehicle interior.

Here, when the imaging device 320 can switch between imaging using visible light and imaging using infrared light, the imaging control unit 210 commands the imaging device 320 to perform imaging using infrared light in a state where no accident is detected by the accident detection unit 110, and commands the imaging device 320 to perform imaging using visible light when an accident is detected by the accident detection unit 110. That is, the imaging control unit 210 commands the imaging device 320 to perform imaging using infrared light until an accident is detected by the accident detection unit 110.

The living body site specifying unit 220 specifies the position of a site of a living body in the vehicle interior using an imaged image.

Specifically, the living body site specifying unit 220 analyzes an imaged image acquired in response to a command of the imaging control unit 210, and specifies the position of the site of the living body in the vehicle interior.

In addition, the living body site specifying unit 220 extracts and outputs an image in a format capable of specifying the site of the living body. Specifically, for example, the living body site specifying unit 220 outputs an imaged image of the specified site together with information indicating the specified site.

FIG. 3 is a diagram illustrating an example of a correspondence relationship between a type of biometric information and a site of a living body.

The living body site specifying unit 220 includes, for example, second data 700 as illustrated in FIG. 3. The second data 700 is information indicating a correspondence relationship between a type of biometric information and a site of a living body.

The living body site specifying unit 220 extracts and outputs an imaged image of a site of a living body corresponding to the type of biometric information selected by the biometric information type selecting unit 131 in the lamp color changing unit 130 by referring to the second data 700.

The site of the living body specified by the living body site specifying unit 220 is, for example, a head, a neck, a chest, an abdomen, a shoulder, or an arm, but is not limited to the above sites as long as the site can be specified from an imaged image.

Note that the head or neck is considered to be a site where damage is most likely to lead to death, and is a site where a ratio of exposure of a bare skin is high. The chest or abdomen is considered to be a site where damage is likely to lead to death.

Note that, in specifying a site by the living body site specifying unit 220, the positions of all sites corresponding to a type of biometric information may be specified, or the sites may be sequentially specified. In specifying a site of a living body, all predetermined sites may be collectively specified, or each type of biometric information selected by the biometric information type selecting unit 131 may be separately specified. For example, when biometric information of a head is acquired, only a site of the head may be specified, and after the biometric information of the head is acquired, only a site of a chest may be specified in order to acquire biometric information of the chest.

Here, an example of a method for specifying a living body site in the living body site specifying unit 220 will be described.

In specifying a body site of an occupant, first, the living body site specifying unit 220 detects an occupant for whom a site of a living body is to be specified. The occupant is detected using a predetermined rule or machine learning from an imaged image as in occupant skeleton detection or occupant face detection. Note that it is conceivable that the occupant takes a posture different from that during normal driving due to damage caused by an accident, and it is difficult to detect the occupant. Therefore, the occupant may be detected using vehicle information acquired from the vehicle sensor 310, or a detection result of the occupant before occurrence of an accident may be used. For example, the determination can be made using a result of skeleton detection or face detection of an infrared light image imaged before occurrence of an accident, or by determining that an occupant is in a seat when seat sensor information is equal to or more than a threshold. In addition, occupant detection accuracy may be further enhanced by using occupant detection information during vehicle traveling, such as information indicating that a vehicle speed or an acceleration is equal to or more than a certain threshold or information indicating that a parking brake is off, obtained from parking brake information.

The biometric information acquiring unit 230 acquires biometric information using an imaged image including a site of a living body specified by the living body site specifying unit 220.

The biometric information acquiring unit 230 receives an imaged image output from the living body site specifying unit 220.

The biometric information acquiring unit 230 analyzes the imaged image and acquires biometric information.

The biometric information acquiring unit 230 outputs the biometric information.

The biometric information is acquired as follows, for example.

Bleeding or complexion: Estimated from whether the color or shape of a specified body site in an imaged image coincides with a predetermined model or from a machine learning result.

Pulse: Acquired by capturing a change in brightness of a face surface considered to be caused by a blood flow of an occupant in an imaged image. Since hemoglobin contained in blood absorbs green light, accuracy of information is increased by adjusting a lamp color to a green wavelength at which a change in brightness can be easily captured.

Respiration: Specified from movement of a specified body site (chest, shoulder, abdomen, or the like) in an imaged image.

The communication control unit 240 causes the communication device 500 to transmit the biometric information acquired by the biometric information acquiring unit 230.

The communication control unit 240 receives the biometric information output from the biometric information acquiring unit 230.

The communication control unit 240 outputs a command signal that is a signal for commanding the communication device to transmit the biometric information together with the biometric information.

When receiving vehicle information from the vehicle information acquiring unit 111, the communication control unit 240 also causes the communication device to transmit the vehicle information.

Here, an example of a hardware configuration that implements the present disclosure will be described.

Figure 4:
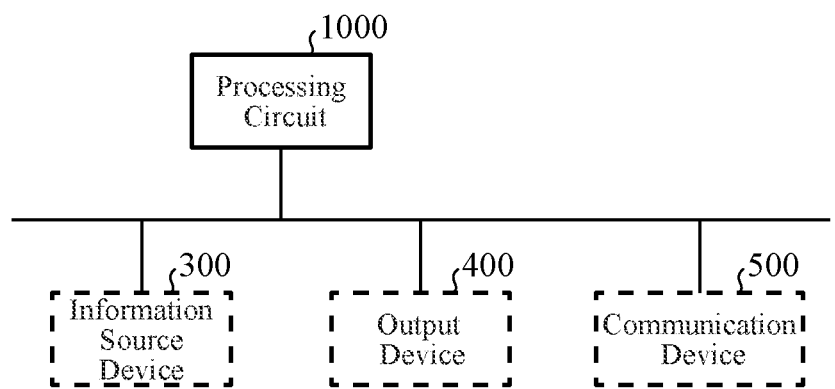
FIG. 4 is a diagram illustrating a first example of a hardware configuration of an illumination control device according to the present disclosure.

FIG. 4 is a diagram illustrating a first example of a hardware configuration of the illumination control device 100 according to the present disclosure and a peripheral device. In FIG. 4, a processing circuit 1000 is connected to the information source device 300, the output device 400, and the communication device 500. The processing circuit 1000 can transmit and receive signals and can transmit and receive information to and from the information source device 300, the output device 400, and the communication device 500.

Figure 5:
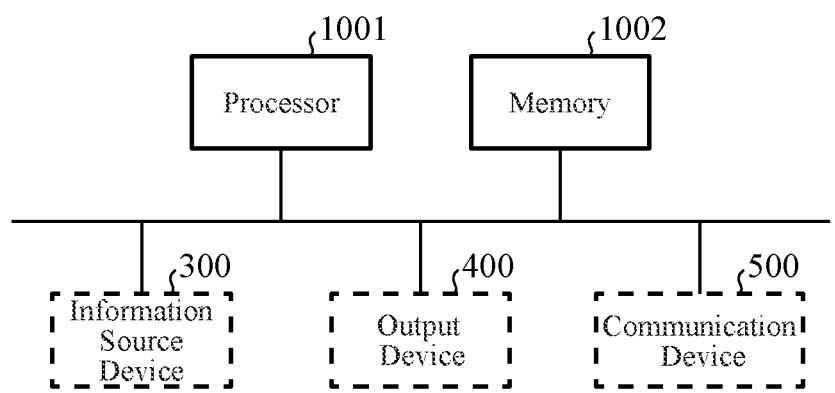
FIG. 5 is a diagram illustrating a second example of the hardware configuration of the illumination control device according to the present disclosure.

FIG. 5 is a diagram illustrating a second example of the hardware configuration of the illumination control device 100 according to the present disclosure and the peripheral device. In FIG. 5, a processor 1001 and a memory 1002 are connected to the information source device 300, the output device 400, and the communication device 500. The processor 1001 can transmit and receive signals and can transmit and receive information to and from the information source device 300, the output device 400, and the communication device 500.

Functions in the illumination control device 100 or the biometric information acquiring device 200 are implemented by a processing circuit.

Specifically, functions of the accident detection unit 110, the vehicle information acquiring unit 111, the accident determination unit 112, the lamp body control unit 120, the lamp color changing unit 130 or a lamp color changing unit 130B described later in a third embodiment, the biometric information type selecting unit 131, the lamp color adjusting unit 132, an external light color specifying unit 133 described later in the third embodiment, an imaging control unit 140 described later in a second embodiment and the third embodiment, a living body site specifying unit 150 described later in the second embodiment and the third embodiment, the biometric information acquiring device 200 or a biometric information acquiring device 200A described later in the second embodiment and the third embodiment, the imaging control unit 210, the living body site specifying unit 220, the biometric information acquiring unit 230, and the communication control unit 240 are implemented by a processing circuit.

Figure 6:
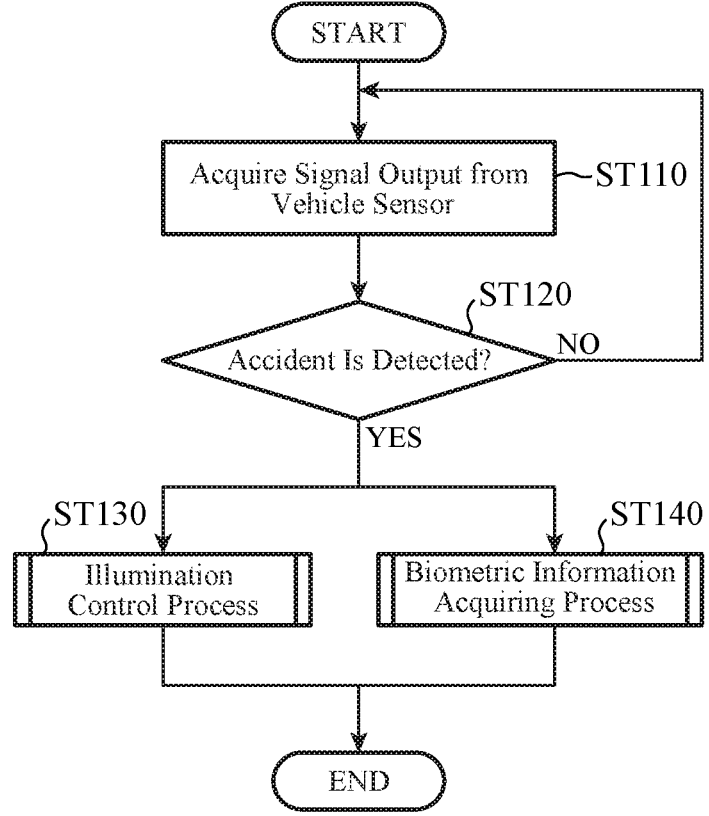
FIG. 6 is a flowchart illustrating a main process of the illumination control device and a main process of a biometric information acquiring device in the present disclosure.

That is, the illumination control device 100 or the biometric information acquiring device 200 includes a processing circuit for executing a series of processes (processes in FIG. 7 to 9, 11, 12, or 14) from step ST110 to step ST140 illustrated in FIG. 6. The processing circuit may be dedicated hardware or a central processing unit (CPU) that executes a program stored in a memory.

When the processing circuit is dedicated hardware illustrated in FIG. 4, for example, a single circuit, a composite circuit, a programmed processor, a parallel programmed processor, an application specific integrated circuit (ASIC), a field-programmable gate array (FPGA), or a combination thereof corresponds to the processing circuit 1000.

Functions of the accident detection unit 110, the vehicle information acquiring unit 111, the accident determination unit 112, the lamp body control unit 120, the lamp color changing unit 130 or the lamp color changing unit 130B described later in the third embodiment, the biometric information type selecting unit 131, the lamp color adjusting unit 132, the external light color specifying unit 133 described later in the third embodiment, the imaging control unit 140 described later in the second embodiment and the third embodiment, the living body site specifying unit 150 described later in the second embodiment and the third embodiment, the biometric information acquiring device 200 or the biometric information acquiring device 200A described later in the second embodiment and the third embodiment, the imaging control unit 210, the living body site specifying unit 220, the biometric information acquiring unit 230, and the communication control unit 240 may be implemented by separate processing circuits, or may be collectively implemented by one processing circuit.

When the processing circuit is the processor 1001 illustrated in FIG. 5, functions of the accident detection unit 110, the vehicle information acquiring unit 111, the accident determination unit 112, the lamp body control unit 120, the lamp color changing unit 130 or the lamp color changing unit 130B described later in the third embodiment, the biometric information type selecting unit 131, the lamp color adjusting unit 132, the external light color specifying unit 133 described later in the third embodiment, the imaging control unit 140 described later in the second embodiment and the third embodiment, the living body site specifying unit 150 described later in the second embodiment and the third embodiment, the biometric information acquiring device 200 or the biometric information acquiring device 200A described later in the second embodiment and the third embodiment, the imaging control unit 210, the living body site specifying unit 220, the biometric information acquiring unit 230, and the communication control unit 240 are implemented by software, firmware, or a combination of software and firmware. Software or firmware is described as a program and stored in the memory 1002.

The processor 1001 reads and executes the program stored in the memory 1002, and thereby implements the functions of the units. That is, the illumination control device 100 includes the memory 1002 for storing a program that causes the above-described series of processes to be executed as a result when the program is executed by the processor 1001. These programs cause a computer to execute a procedure or a method for implementing functions of the accident detection unit 110, the vehicle information acquiring unit 111, the accident determination unit 112, the lamp body control unit 120, the lamp color changing unit 130 or the lamp color changing unit 130B described later in the third embodiment, the biometric information type selecting unit 131, the lamp color adjusting unit 132, the external light color specifying unit 133 described later in the third embodiment, the imaging control unit 140 described later in the second embodiment and the third embodiment, the living body site specifying unit 150 described later in the second embodiment and the third embodiment, the biometric information acquiring device 200 or the biometric information acquiring device 200A described later in the second embodiment and the third embodiment, the imaging control unit 210, the living body site specifying unit 220, the biometric information acquiring unit 230, and the communication control unit 240.

To the memory 1002, for example, a nonvolatile or volatile semiconductor memory such as a random access memory (RAM), a read only memory (ROM), a flash memory, an erasable programmable read only memory (EPROM), or an electrically-EPROM (EEPROM), a magnetic disk, a flexible disk, an optical disc, a compact disc, a mini disc, a DVD, or the like corresponds.

Some of the functions of the accident detection unit 110, the vehicle information acquiring unit 111, the accident determination unit 112, the lamp body control unit 120, the lamp color changing unit 130 or the lamp color changing unit 130B described later in the third embodiment, the biometric information type selecting unit 131, the lamp color adjusting unit 132, the external light color specifying unit 133 described later in the third embodiment, an imaging control unit 140 described later in the second embodiment and the third embodiment, the living body site specifying unit 150 described later in the second embodiment and the third embodiment, the biometric information acquiring device 200 or the biometric information acquiring device 200A described later in the second embodiment and the third embodiment, the imaging control unit 210, the living body site specifying unit 220, the biometric information acquiring unit 230, and the communication control unit 240 may be implemented by dedicated hardware, and some thereof may be implemented by software or firmware. For example, the function of the vehicle information acquiring unit 111 may be implemented by the processing circuit 1000 as dedicated hardware, and the function of the accident detection unit 110 may be implemented by the processor 1001 reading and executing a program stored in the memory 1002.

As described above, the processing circuit can implement each of the above functions by hardware, software, firmware, or a combination thereof.

Processes according to the present disclosure will be described.

FIG. 6 is a flowchart illustrating a main process of the illumination control device 100 and a main process of the biometric information acquiring device 200 in the present disclosure.

Figure 7:
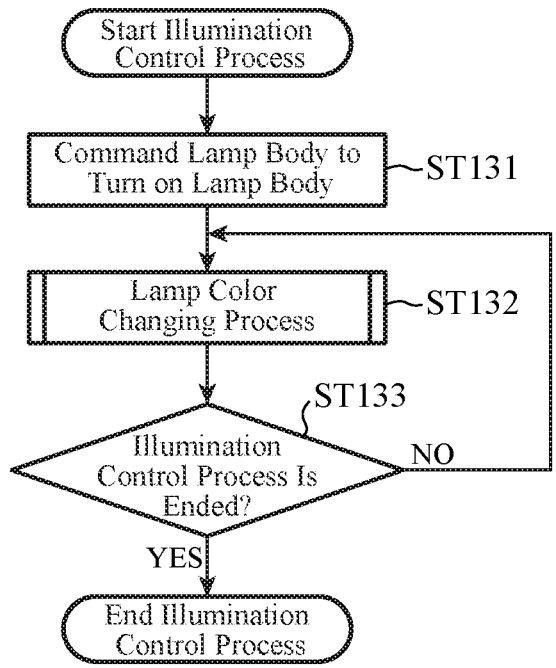
FIG. 7 is a flowchart illustrating an example of an illumination control process illustrated in FIG. 6.

FIG. 7 is a flowchart illustrating an example of an illumination control process illustrated in FIG. 6.

Figure 8:
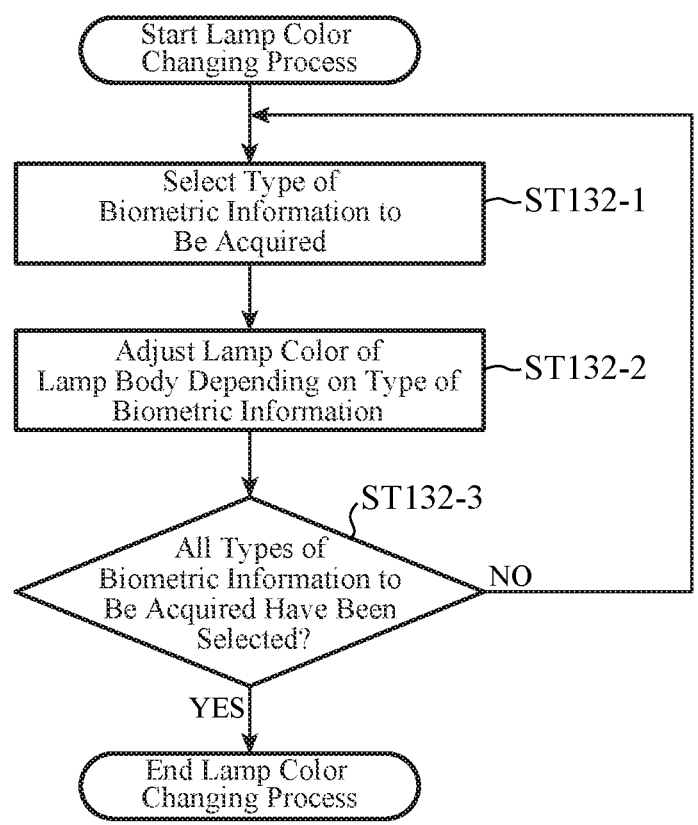
FIG. 8 is a flowchart illustrating an example of a lamp color changing process illustrated in FIG. 7.

FIG. 8 is a flowchart illustrating an example of a lamp color changing process illustrated in FIG. 7.

Figure 9:
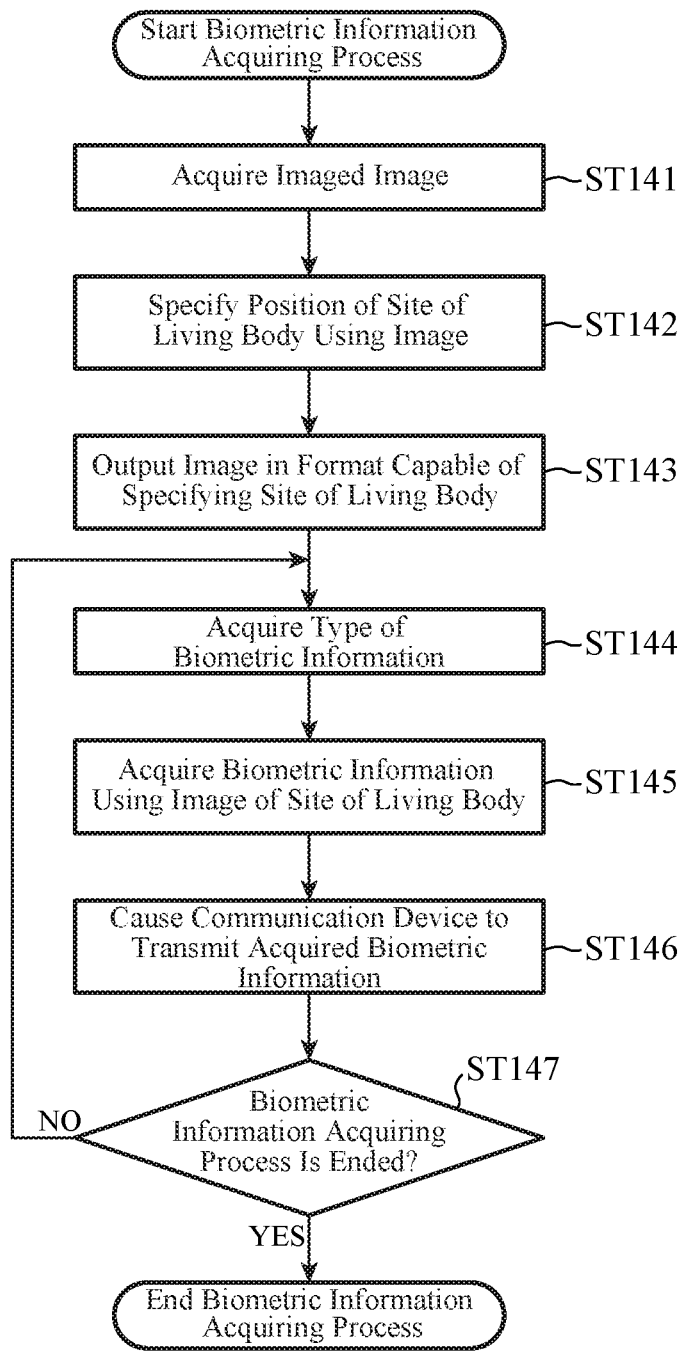
FIG. 9 is a flowchart illustrating an example of a biometric information acquiring process illustrated in FIG. 6.

FIG. 9 is a flowchart illustrating an example of a biometric information acquiring process illustrated in FIG. 6.

The illumination control device 100 starts a process, for example, at a timing when an engine is started in the vehicle ("Start" in FIG. 6).

The accident detection unit 110 waits until acquiring a signal output from the vehicle sensor 310, and starts a process when acquiring the signal output from the vehicle sensor 310 (step ST110).

The accident detection unit 110 determines occurrence of an accident using vehicle information indicated by the acquired signal, and detects the accident when determining that the accident has occurred.

Specifically, the vehicle information acquiring unit 111 in the accident detection unit 110 acquires a signal output from the vehicle sensor 310, and transmits vehicle information indicated by the acquired signal to the accident determination unit 112.

In addition, the vehicle information acquiring unit 111 outputs the vehicle information to the communication control unit 240.

The accident determination unit 112 in the accident detection unit 110 determines occurrence of an accident using the vehicle information.

When determining that an accident has occurred, the accident determination unit 112 outputs an accident detection signal to each of the lamp body control unit 120, the biometric information type selecting unit 131, and the imaging control unit 210.

In a state where no accident is detected (step ST120 "NO"), the accident detection unit 110 repeats the processes from step ST110.

When the accident detection unit 110 detects an accident (step ST120 "YES"), an illumination control process (step ST130) and a biometric information acquiring process (step ST140) are executed.

In the configuration illustrated in FIG. 1, the illumination control device 100 executes the illumination control process (step ST130), and the biometric information acquiring device 200 executes the biometric information acquiring process (step ST140).

When the process in step ST130 and the process in step ST140 end, the process is ended ("End" in FIG. 6).

Details of the illumination control process (step ST130) will be described.

In the illumination control device 100, when the accident detection unit 110 outputs an accident detection signal, an illumination control process is started (Start illumination control process in FIG. 7).

The lamp body control unit 120 waits until receiving the accident detection signal output from the accident detection unit 110.

When receiving the accident detection signal output from the accident detection unit 110, the lamp body control unit 120 commands the lamp body 410 to turn on the lamp body 410 (step ST131).

The lamp color changing unit 130 waits until receiving the accident detection signal output from the accident detection unit 110.

When receiving the accident detection signal output from the accident detection unit 110, the lamp color changing unit 130 proceeds to a lamp color changing process (step ST132).

When the lamp color changing unit 130 ends the lamp color changing process (step ST132), the control unit (not illustrated) in the illumination control device 100 determines whether to end the illumination control process (step ST133).

For example, when receiving a command to stop the process from the outside. the control unit determines to end the illumination control process.

When determining not to end the illumination control process (step ST133 "NO"), the illumination control device 100 repeats the lamp color changing process (step ST132).

When determining to end the illumination control process (step ST133 "YES"), the illumination control device 100 ends the illumination control process (End illumination control process in FIG. 7).

Details of the lamp color changing process (step ST132) will be described.

The lamp color changing unit 130 starts the lamp color changing process ("Start lamp color changing process" in FIG. 8).

The biometric information type selecting unit 131 in the lamp color changing unit 130 selects a type of biometric information to be acquired (step ST132-1).

The lamp color adjusting unit 132 in the lamp color changing unit 130 adjusts a lamp color of the lamp body 410 depending on the type of biometric information (step ST132-2).

The control unit (not illustrated) determines whether all types of biometric information to be acquired have been selected (step ST132-3).

When the control unit (not illustrated) determines that not all types of biometric information to be acquired have been selected (step ST132-3 "NO"), the control unit performs control to repeat the processes from step ST132-1.

When the control unit (not illustrated) determines that all types of biometric information to be acquired have been selected (step ST132-3 "YES"), the control unit controls to end the lamp color changing process ("End lamp color changing process" in FIG. 8).

Details of the biometric information acquiring process (step ST140) will be described.

The biometric information acquiring device 200 starts the biometric information acquiring process ("Start biometric information acquiring process" in FIG. 9). The biometric information acquiring device 200 starts the biometric information acquiring process, for example, when receiving an accident detection signal from the accident determination unit 112 or when receiving an imaged image from the imaging device 320.

The living body site specifying unit 220 acquires an imaged image acquired by the imaging device 320 (step ST141).

The living body site specifying unit 220 specifies the position of a site of a living body using the imaged image (step ST142).

The living body site specifying unit 220 extracts and outputs an image in a format capable of specifying the site of the living body (step ST143).

The living body site specifying unit 220 acquires a type of biometric information (step ST144).

The biometric information acquiring unit 230 acquires biometric information using the type of biometric information and the image of the site of the living body (step ST145).

The communication control unit 240 causes the communication device to transmit the biometric information acquired by the biometric information acquiring unit 230 (step ST146).

The control unit (not illustrated) determines whether the biometric information acquiring process is ended (step ST147).

When determining that the biometric information acquiring process is not ended (step ST147 "NO"), the control unit performs control to repeat the processes from step ST144.

When determining that the biometric information acquiring process is ended (step ST147 "YES"), the control unit controls to end the biometric information acquiring process ("End biometric information acquiring process" in FIG. 9).

Here, one modification of the first embodiment will be described.

The present disclosure does not exclude that the illumination control device 100 and the biometric information acquiring device 200 are integrally constituted.

The illumination control device 100 may include some or all of the components of the biometric information acquiring device 200.

In addition, the biometric information acquiring device 200 may include some or all of the components of the illumination control device 100.

As described above, the illumination control device according to the present disclosure includes: an accident detection unit to detect an accident of a vehicle using a signal output from a sensor mounted on the vehicle; a lamp body control unit to command a lamp body that illuminates a vehicle interior using visible light to turn on when an accident is detected by the accident detection unit; and a lamp color changing unit to change a lamp color of the lamp body when an accident is detected by the accident detection unit.

As a result, it is possible to provide an illumination control device that controls illumination in such a manner that biometric information can be obtained without depending on imaging conditions when a vehicle accident occurs.

In the illumination control device according to the present disclosure, the lamp color changing unit includes: a biometric information type selecting unit to select a type of biometric information to be acquired by referring to type information indicating a type of biometric information stored in advance when an accident is detected by the accident detection unit; and a lamp color adjusting unit to adjust a lamp color of the lamp body depending on the type of biometric information selected by the biometric information type selecting unit.

As a result, it is possible to provide an illumination control device capable of adjusting the lamp color of the lamp body depending on the type of biometric information.

In the illumination control device according to the present disclosure, when the type of biometric information selected by the biometric information type selecting unit is a pulse, the lamp color adjusting unit performs adjustment in such a manner that a wavelength of the lamp color is equal to or more than 490 nm and equal to or less than 570 nm.

As a result, it is possible to provide an illumination control device capable of accurately acquiring a pulse.

In the illumination control device according to the present disclosure, an imaging control unit commands an imaging device to perform imaging using infrared light until an accident is detected by the accident detection unit.

As a result, it is possible to provide an illumination control device capable of imaging a vehicle interior using infrared light in a state where no accident occurs.

As described above, the biometric information acquiring device according to the present disclosure includes: an accident detection unit to detect an accident of a vehicle using a signal output from a sensor mounted on the vehicle; a lamp body control unit to command a lamp body that illuminates a vehicle interior using visible light to turn on when an accident is detected by the accident detection unit; a lamp color changing unit to change a lamp color of the lamp body when an accident is detected by the accident detection unit; an imaging control unit to command an imaging device that performs imaging using visible light to image the vehicle interior when an accident is detected by the accident detection unit; a living body site specifying unit to specify the position of a site of a living body in the vehicle interior using an imaged image acquired in response to a command of the imaging control unit; a biometric information acquiring unit to acquire biometric information using an imaged image including the site of the living body specified by the living body site specifying unit; and a communication control unit to cause a communication device to transmit biometric information acquired by the biometric information acquiring unit.

As a result, it is possible to provide a biometric information acquiring device capable of obtaining biometric information without depending on imaging conditions when a vehicle accident occurs.

As described above, the illumination control method according to the present disclosure includes: an accident detection step of detecting, by an accident detection unit, an accident of a vehicle using a signal output from a sensor mounted on the vehicle; a lamp body control step of commanding, by a lamp body control unit, a lamp body that illuminates a vehicle interior using visible light to turn on the lamp body when an accident is detected by the accident detection unit; and a lamp color changing step of changing, by a lamp color changing unit, a lamp color of the lamp body when an accident is detected by the accident detection unit.

As a result, an illumination control device that controls illumination in such a manner that biometric information can be obtained without depending on imaging conditions when a vehicle accident occurs can be implemented using a computer or the like.

Second Embodiment

A second embodiment is a mode in which an illumination control device includes an imaging control unit 140 and a living body site specifying unit 150, and further adjusts light distribution with respect to the position of a site of a living body.

Figure 10:
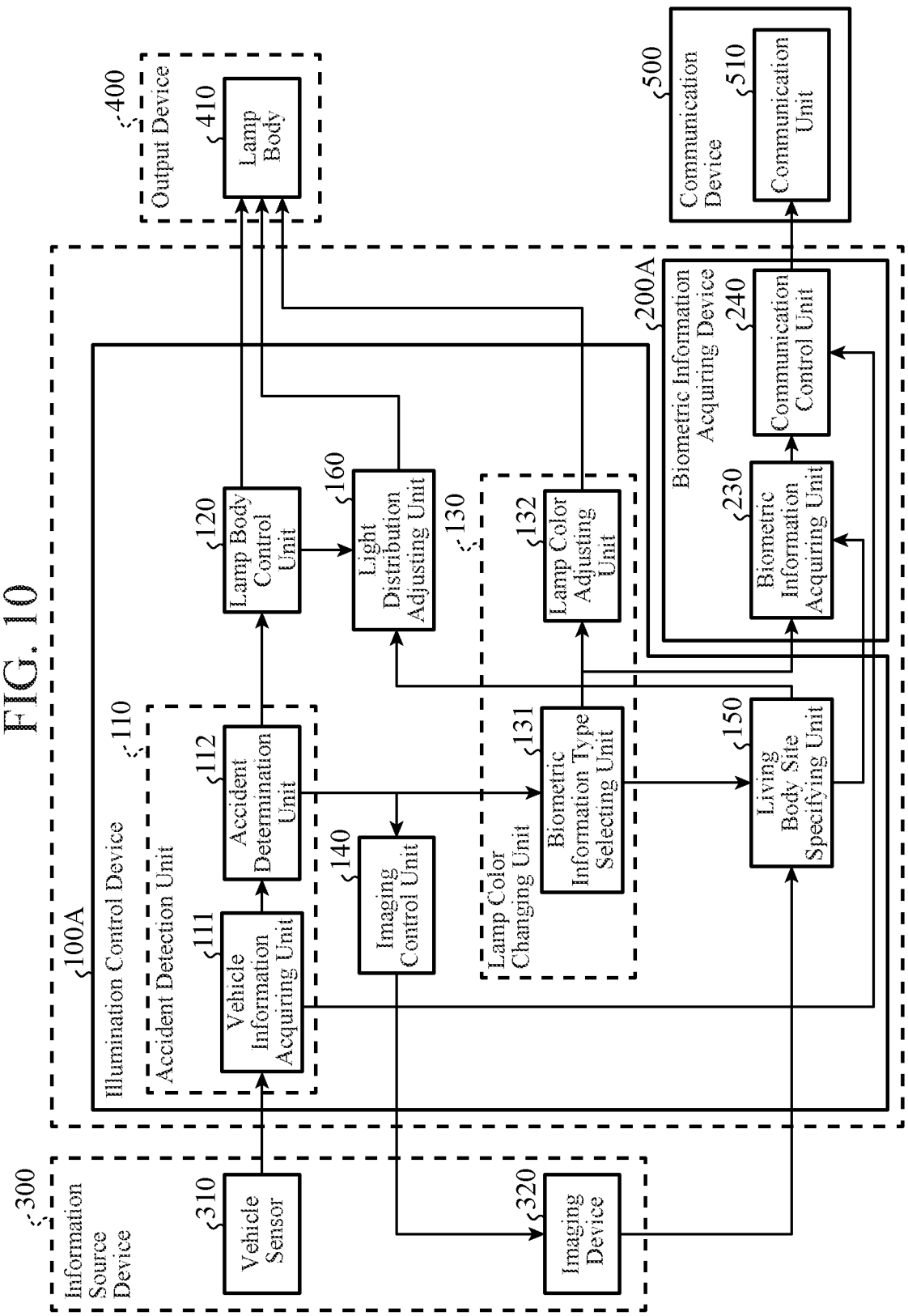
FIG. 10 is a block diagram illustrating a configuration of an illumination control device according to a second embodiment and a peripheral device related thereto.

FIG. 10 is a block diagram illustrating a configuration of an illumination control device 100A according to the second embodiment and a peripheral device related thereto.

The illumination control device 100A illustrated in FIG. 10 includes the imaging control unit 140 and the living body site specifying unit 150. In addition, the illumination control device 100A includes a light distribution adjusting unit 160.

The imaging control unit 140 has a configuration similar to that of the imaging control unit 210 illustrated in FIG. 1, and detailed description thereof is omitted.

In the second embodiment, specifically, when an accident of a vehicle occurs, the imaging device 320 receives a command from the imaging control unit 140 of the illumination control device 100A and images a vehicle interior.

In addition to the function of the living body site specifying unit 220 illustrated in FIG. 1, when the position of a site of a living body in the vehicle interior cannot be specified, the living body site specifying unit 150 outputs a specification impossible signal, which is a signal indicating that the position of the site of the living body cannot be specified, to the light distribution adjusting unit 160.

In addition, when the position of the site of the living body in the vehicle interior cannot be specified, the living body site specifying unit 150 estimates the position of the site of the living body.

In addition, the living body site specifying unit 150 adjusts light distribution in such a manner that brightness of the estimated position of the site of the living body falls within a range between a first threshold and a second threshold.

In addition, when a biometric information acquiring unit 230 cannot acquire biometric information, the living body site specifying unit 150 changes the first threshold or the second threshold.

When the living body site specifying unit 150 cannot specify the position of the site of the living body in the vehicle interior, the light distribution adjusting unit 160 estimates the position of the site of the living body in the vehicle interior and commands a lamp body 410 to adjust light distribution with respect to the estimated position of the site of the living body.

Specifically, when receiving a specification impossible signal from the living body site specifying unit 150, the light distribution adjusting unit 160 estimates the position of the site of the living body in the vehicle interior.

The light distribution adjusting unit 160 outputs a command signal that commands the lamp body 410 to adjust light distribution with respect to the estimated position of the site of the living body.

For example, the light distribution adjusting unit 160 adjusts light distribution of visible light output from the lamp body 410 in such a manner that brightness of a site of a place where a body site is considered to be present is within a predetermined range by a predetermined method such as occupant skeleton detection.

The adjustment of light distribution performed by the light distribution adjusting unit 160 includes at least one of the following three.

(1) Selection of lamp body 410: A lamp body to be turned on or off is selected from among a plurality of lamp bodies that illuminates a vehicle interior.

(2) Selection of light source in lamp body: A light source to be lighted is selected from among a plurality of light sources (for example, LEDs) in a lamp body.

(3) Light control of light source: Brightness of a light source is controlled.

The adjustment of light distribution is determined in advance on the basis of, for example, a light control simulation result by a combination of the above (1), (2), and (3) performed at the time of optical design.

The above (1), (2), and (3) are determined by referring to the simulation result depending on position information of a place where the body site is present or is estimated to be present, and brightness thereof.

An example of adjustment of light distribution will be described.

For example, when the brightness of the site specified by the living body site specifying unit 150 is equal to or more than a threshold and is too bright, the light distribution adjusting unit 160 controls light in such a manner that light distribution corresponding to the site decreases depending on a determination result, or increases light distribution behind the site. As a result, the brightness of the site is set to fall within a range between the first threshold and the second threshold.

In addition, for example, when the brightness of the site specified by the living body site specifying unit 150 is equal to or less than the threshold and is too dark, the light distribution adjusting unit 160 controls light in such a manner that light distribution corresponding to the site increases depending on the determination result.

Details of an illumination control process will be described.

Figure 11:
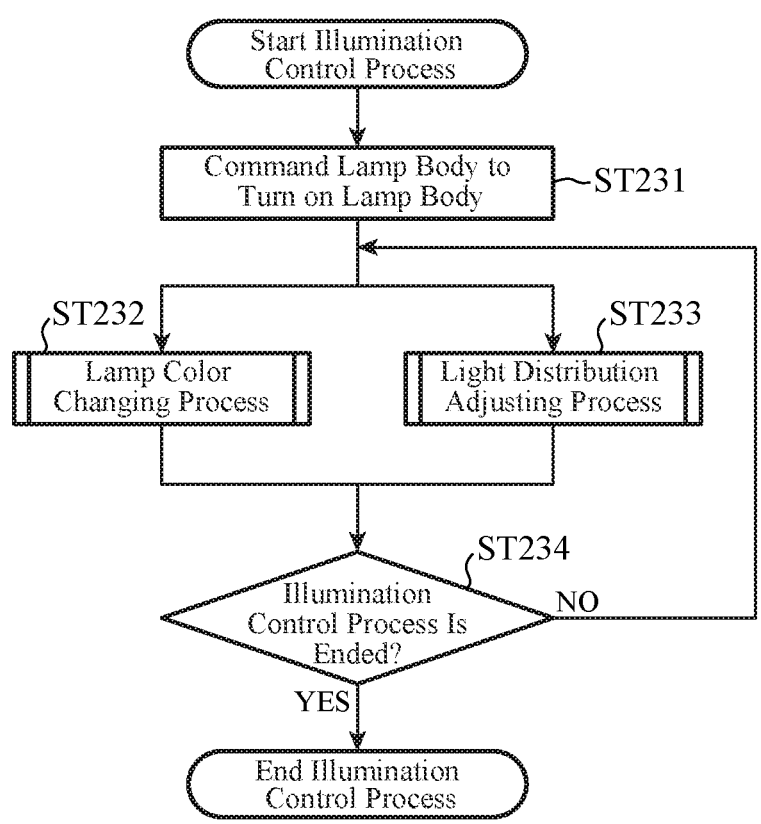
FIG. 11 is a flowchart illustrating an example of an illumination control process according to the second embodiment.

FIG. 11 is a flowchart illustrating an example of the illumination control process according to the second embodiment.

In the illumination control device 100A, when an accident detection unit 110 outputs an accident detection signal, the illumination control process is started ("Start illumination control process" in FIG. 11).

The lamp body control unit 120 waits until receiving the accident detection signal output from the accident detection unit 110.

When receiving the accident detection signal output from the accident detection unit 110, the lamp body control unit 120 commands the lamp body 410 to turn on the lamp body 410 (step ST231).

The lamp color changing unit 130 waits until receiving the accident detection signal output from the accident detection unit 110.

When receiving the accident detection signal output from the accident detection unit 110, the lamp color changing unit 130 proceeds to a lamp color changing process (step ST232) or a light distribution adjusting process (step ST233).

When the lamp color changing unit 130 ends the lamp color changing process (step ST232) or the light distribution adjusting process (step ST233), a control unit (not illustrated) in the illumination control device 100A determines whether to end the illumination control process (step ST234).

For example, when receiving a command to stop the process from the outside, the control unit determines to end the illumination control process.

When determining not to end the illumination control process (step ST234 "NO"), the illumination control device 100A repeats the lamp color changing process (step ST232) or the light distribution adjusting process (step ST233).

When determining to end the illumination control process (step ST234 "YES"), the illumination control device 100A ends the illumination control process ("End illumination control process" in FIG. 11).

Details of the lamp color changing process (step ST232) are similar to those in FIG. 8, and thus description thereof is omitted.

Details of the light distribution adjusting process (step ST233) will be described.

Figure 12:
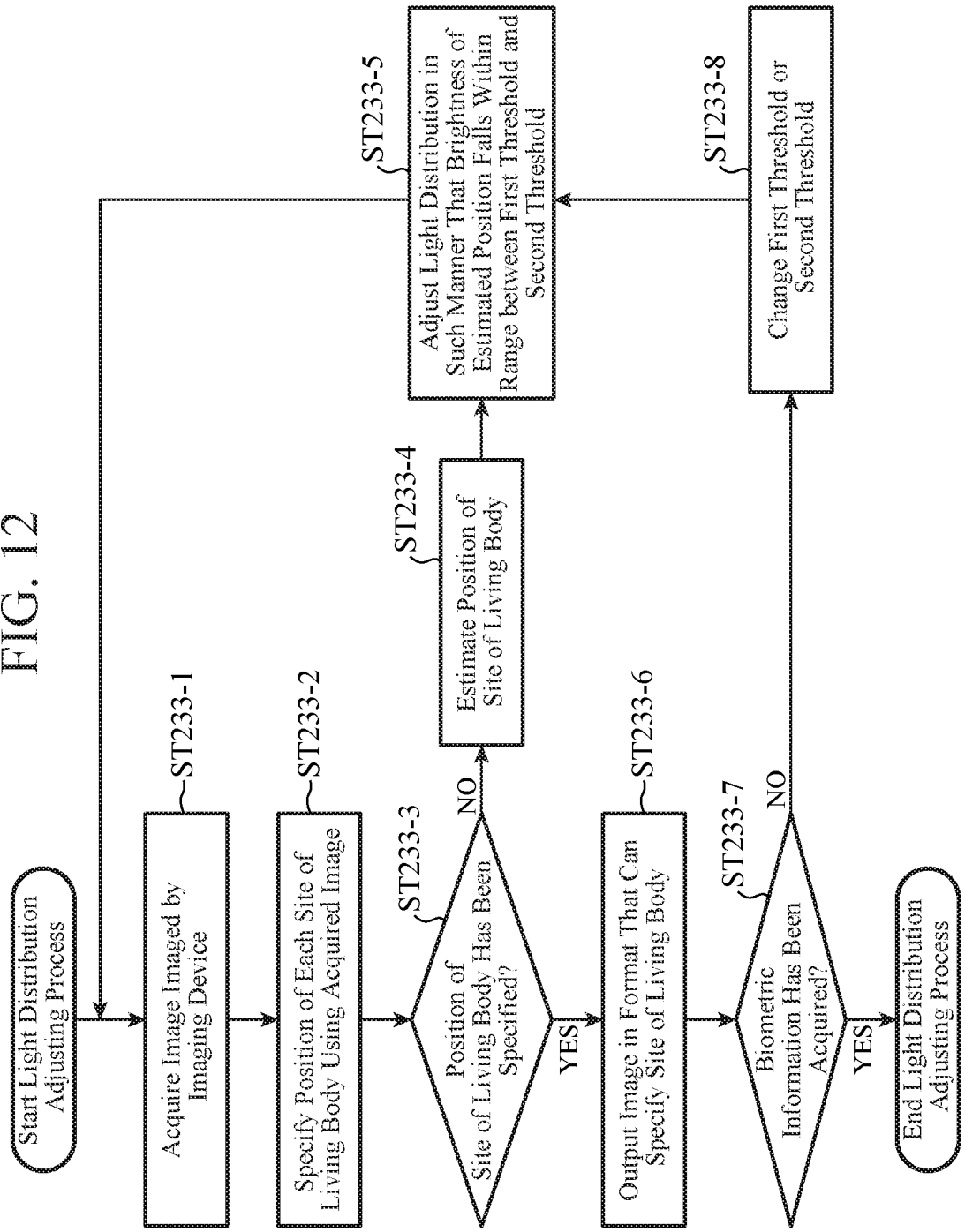
FIG. 12 is a flowchart illustrating an example of a light distribution adjusting process illustrated in FIG. 11.

FIG. 12 is a flowchart illustrating an example of the light distribution adjusting process illustrated in FIG. 11.

The illumination control device 100A starts the light distribution adjusting process ("Start light distribution adjusting process" in FIG. 12).

The living body site specifying unit 150 acquires an image imaged by the imaging device 320 (step ST233-1).

The living body site specifying unit 150 specifies the position of each site of a living body using the acquired image (step ST233-2).

The living body site specifying unit 150 determines whether the position of the site of the living body has been specified (step ST233-3).

When determining that the position of the site of the living body cannot be specified (step ST233-3 "NO"), the living body site specifying unit 150 estimates the position of the site of the living body (step ST233-4).

When step ST233-4 is executed, the process proceeds to step ST233-5.

In step ST233-5, the light distribution adjusting unit 160 adjusts light distribution in such a manner that brightness of the estimated position falls within a range between the first threshold and the second threshold.

When determining that the position of the site of the living body has been specified (step ST233-3 "YES"), the living body site specifying unit 150 outputs an image in a format capable of specifying the site of the living body to the biometric information acquiring unit 230 (step ST233-6).

The living body site specifying unit 150 determines whether biometric information has been acquired by the biometric information acquiring unit 230 (step ST233-7).

When the biometric information acquiring unit 230 determines that the biometric information cannot be acquired (step ST233-7 "NO"), the living body site specifying unit 150 changes the first threshold or the second threshold and proceeds to step ST233-5.

After step ST233-5 is executed, the processes are repeated from step ST233-1.

When the biometric information acquiring unit 230 determines that biometric information has been acquired (step ST233-7 "YES"), the light distribution adjusting process is ended ("End light distribution adjusting process" in FIG. 12). Here, one modification of the second embodiment will be described.

The present disclosure does not exclude that the illumination control device 100A and the biometric information acquiring device 200A are integrally constituted.

The illumination control device 100A may include some or all of the components of the biometric information acquiring device 200A.

In addition, the biometric information acquiring device 200A may include some or all of the components of the illumination control device 100A.

The illumination control device according to the present disclosure further includes: an imaging control unit to command an imaging device that performs imaging using visible light to image a vehicle interior when an accident is detected by an accident detection unit; a living body site specifying unit to specify the position of a site of a living body in the vehicle interior using an imaged image acquired in response to a command of the imaging control unit; and a light distribution adjusting unit to estimate the position of the site of the living body in the vehicle interior and commands a lamp body to adjust light distribution with respect to the estimated position of the site of the living body when the living body site specifying unit cannot specify the position of the site of the living body in the vehicle interior.

As a result, it is possible to provide an illumination control device that controls illumination in such a manner that biometric information can be obtained more accurately without depending on imaging conditions when a vehicle accident occurs.

As described above, the biometric information acquiring device according to the present disclosure further includes the light distribution adjusting unit to estimate the position of a site of a living body in a vehicle interior and commands a lamp body to adjust light distribution with respect to the estimated position of the site of the living body when the living body site specifying unit 220 cannot specify the position of the site of the living body in the vehicle interior.

As a result, it is possible to provide a biometric information acquiring device capable of obtaining biometric information more accurately without depending on imaging conditions when a vehicle accident occurs.

Third Embodiment

A third embodiment is a mode in which illumination with an influence of external light removed is performed.

Figure 13:
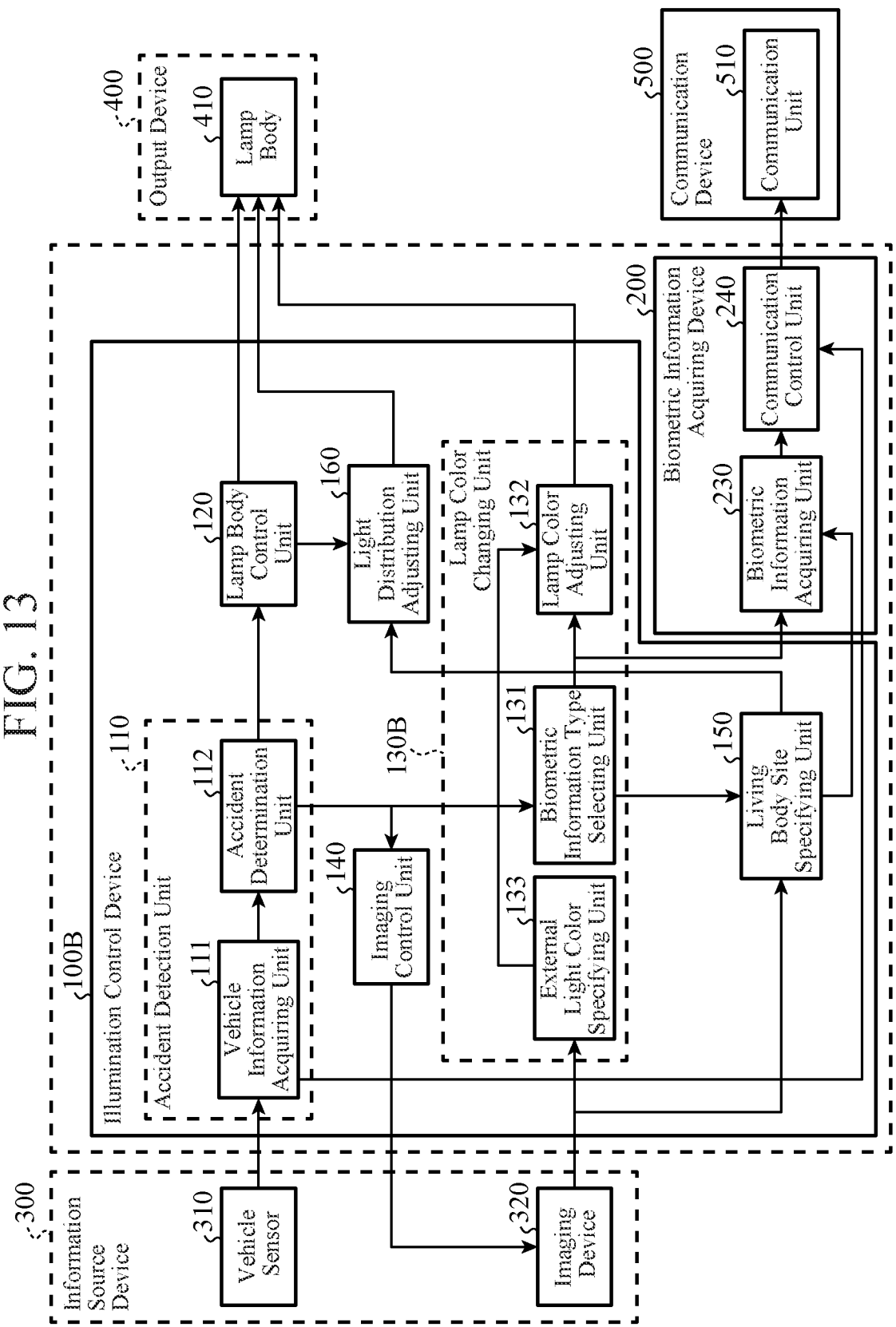
FIG. 13 is a block diagram illustrating a configuration of an illumination control device according to a third embodiment and a peripheral device related thereto.

FIG. 13 is a block diagram illustrating a configuration of an illumination control device 100B according to the third embodiment and a peripheral device related thereto.

The illumination control device 100B illustrated in FIG. 13 is the illumination control device 100A illustrated in FIG. 10, in which the lamp color changing unit 130 further includes an external light color specifying unit 133.

Among components similar to those of the illumination control device 100A illustrated in FIG. 10, description of the components described above is omitted.

The external light color specifying unit 133 specifies a color of external light incident on a vehicle interior using an imaged image acquired by the imaging device 320 and lamp color information indicating a lamp color of a lamp body 410A.

When a type of biometric information selected by the biometric information type selecting unit 131 is a bleeding state or a complexion, the lamp color adjusting unit 132 performs adjustment in such a manner that a lamp color of the lamp body 410A is a color obtained by subtracting the color of external light from the color indicated by the lamp color information.

Figure 14:
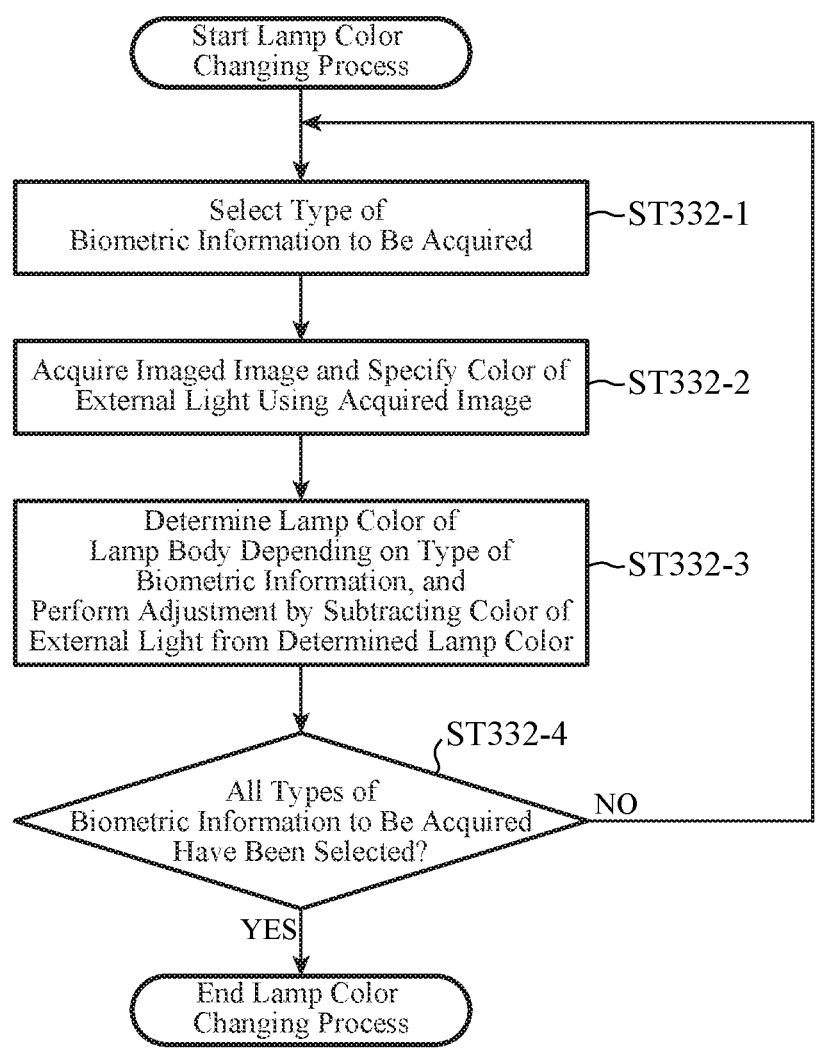
FIG. 14 is a flowchart illustrating an example of a lamp color changing process according to the third embodiment.

FIG. 14 is a flowchart illustrating an example of a lamp color changing process according to the third embodiment.

The lamp color changing unit 130 starts the lamp color changing process ("Start lamp color changing process" in FIG. 14).

The biometric information type selecting unit 131 in the lamp color changing unit 130 selects a type of biometric information to be acquired (step ST332-1).

The external light color specifying unit 133 acquires an imaged image and specifies the color of external light using the acquired image (step ST332-2).

The lamp color of the lamp body 410 is determined depending on a type of biometric information, and adjustment is performed by subtracting the color of external light from the determined lamp color (step ST332-3).

A control unit (not illustrated) determines whether all types of biometric information to be acquired have been selected (step ST332-4).

When the control unit (not illustrated) determines that not all types of biometric information to be acquired have been selected (step ST332-4 "NO"), the control unit performs control to repeat the processes from step ST332-1.

When the control unit (not illustrated) determines that all types of biometric information to be acquired have been selected (step ST332-4 "YES"), the control unit controls to end the lamp color changing process ("End lamp color changing process" in FIG. 14).

In the illumination control device according to the present disclosure, the lamp color changing unit further includes an external light color specifying unit to specify a color of external light incident on a vehicle interior using an imaged image acquired by an imaging device and lamp color information indicating a lamp color of a lamp body, and the lamp color adjusting unit performs adjustment in such a manner that the lamp color of the lamp body is a color obtained by subtracting the color of the external light from the color indicated by the lamp color information when the type of biometric information selected by the biometric information type selecting unit is a bleeding state or a complexion.

As a result, it is possible to further provide an illumination control device capable of easily imaging and illuminating a site of a living body.

Note that the embodiments of the present disclosure can be freely combined with one another, any component in each of the embodiments can be modified, or any component in each of the embodiments can be omitted within the scope of the present disclosure.

INDUSTRIAL APPLICABILITY

The illumination control device according to the present disclosure is suitable for use in an illumination control device for a vehicle or the like.

REFERENCE SIGNS LIST

100, 100A, 100B: illumination control device, 110: accident detection unit, 111: vehicle information acquiring unit, 112: accident determination unit, 120: lamp body control unit, 130, 130B: lamp color changing unit, 131: biometric information type selecting unit, 132: lamp color adjusting unit, 133: external light color specifying unit, 140: imaging control unit, 150: living body site specifying unit, 200, 200A: biometric information acquiring device, 210: imaging control unit, 220: living body site specifying unit, 230: biometric information acquiring unit, 240: communication control unit, 300: information source device, 310: vehicle sensor, 320: imaging device, 400, 400A: output device, 410, 410A: lamp body, 500: communication device, 510: communication unit, 600: first data, 700: second data, 1000: processing circuit, 1001: processor, 1002: memory

The invention claimed is:

1. An illumination control device comprising:
processing circuitry configured to
detect an accident of a vehicle using a signal output from a sensor mounted on the vehicle;
command a lamp body that illuminates a vehicle interior using visible light to turn on when an accident is detected;
change a lamp color of the lamp body when the accident is detected;
command an imaging device that performs imaging using visible light to image a vehicle interior when the accident is detected;

specify a position of a site of a living body in the vehicle interior using an imaged image acquired in response to the command; and estimate the position of the site of the living body in the vehicle interior and command the lamp body to adjust light distribution with respect to the estimated position of the site of the living body when the position of the site of the living body in the vehicle interior is not specified.

2. The illumination control device according to claim 1, wherein the processing circuitry is further configured to select a type of biometric information to be acquired by referring to type information indicating types of biometric information stored in advance when the accident is detected; and adjust the lamp color of the lamp body depending on the type of biometric information having been selected.

3. The illumination control device according to claim 2, wherein when the type of biometric information selected is a pulse, the processing circuitry performs adjustment in such a manner that a wavelength of the lamp color is equal to or more than 490 nm and equal to or less than 570 nm.

4. The illumination control device according to claim 2, wherein the processing circuitry is further configured to specify a color of external light incident on the vehicle interior using the imaged image acquired by the imaging device and lamp color information indicating a lamp color of the lamp body; and perform adjustment in such a manner that the lamp color of the lamp body turns into a color obtained by subtracting the color of the external light from the color indicated by the lamp color information when the type of biometric information having been selected is a bleeding state or a complexion.

5. The illumination control device according to claim 1, wherein the processing circuitry commands the imaging device to perform imaging using infrared light until an accident is detected.

6. An illumination control device comprising:

processing circuitry configured to detect an accident of a vehicle using a signal output from a sensor mounted on the vehicle;

command a lamp body that illuminates a vehicle interior using visible light to turn on when an accident is detected; and change a lamp color of the lamp body when the accident is detected;

select a type of biometric information to be acquired by referring to type information indicating types of biometric information stored in advance when the accident is detected;

adjust the lamp color of the lamp body depending on the type of biometric information having been selected; and specify a color of external light incident on the vehicle interior using the imaged image acquired by the imaging device and lamp color information indicating a lamp color of the lamp body; and perform adjustment in such a manner that the lamp color of the lamp body turns into a color obtained by subtracting the color of the external light from the color indicated by the lamp color information when the type of biometric information having been selected is a bleeding state or a complexion.

7. A biometric information acquiring device comprising:

processing circuitry configured to detect an accident of a vehicle using a signal output from a sensor mounted on the vehicle;

command a lamp body that illuminates a vehicle interior using visible light to turn on when an accident is detected;

change a lamp color of the lamp body when the accident is detected;

command an imaging device that performs imaging using visible light to image the vehicle interior when the accident is detected;

specify a position of a site of a living body in the vehicle interior using an imaged image acquired in response to the command;

acquire biometric information using the imaged image including the specified site of the living body;

cause a communication device to transmit the biometric information having been acquired; and estimate the position of the site of the living body in the vehicle interior and command the lamp body to adjust light distribution with respect to the estimated position of the site of the living body when the position of the site of the living body in the vehicle interior is not specified.

8. An illumination control method comprising:

Detecting an accident of a vehicle using a signal output from a sensor mounted on the vehicle;

Commanding a lamp body that illuminates a vehicle interior using visible light to turn on when an accident is detected;

changing a lamp color of the lamp body when the accident is detected;

commanding an imaging device that performs imaging using visible light to image a vehicle interior when the accident is detected;

specifying a position of a site of a living body in the vehicle interior using an imaged image acquired in response to the command; and estimating the position of the site of the living body in the vehicle interior and commanding the lamp body to adjust light distribution with respect to the estimated position of the site of the living body when the position of the site of the living body in the vehicle interior is not specified.

9. An illumination control method comprising:

detecting an accident of a vehicle using a signal output from a sensor mounted on the vehicle;

commanding a lamp body that illuminates a vehicle interior using visible light to turn on when an accident is detected;

changing a lamp color of the lamp body when the accident is detected;

selecting a type of biometric information to be acquired by referring to type information indicating types of biometric information stored in advance when the accident is detected;

adjusting the lamp color of the lamp body depending on the type of biometric information having been selected;

specifying a color of external light incident on the vehicle interior using the imaged image acquired by the imaging device and lamp color information indicating a lamp color of the lamp body; and performing adjustment in such a manner that the lamp color of the lamp body turns into a color obtained by subtracting the color of the external light from the color indicated by the lamp color information when the type of biometric information having been selected is a bleeding state or a complexion.

\* \* \* \* \*